United States Patent
Hoffman (10) Patent No.: US 7,050,529 B2
(45) Date of Patent: May 23, 2006

(54) METHODS AND APPARATUS FOR PERFORMING A COMPUTED TOMOGRAPHY SCAN

(75) Inventor: David M. Hoffman, New Berlin, WI (US)

(73) Assignee: GE Medical Systems Global Technolgy Company, LLC, Waukesha, WI (US)

( * ) Notice: Subject to any disclaimer, the term of this patent is extended or adjusted under 35 U.S.C. 154(b) by 0 days.

(21) Appl. No.: 10/064,511

(22) Filed: Jul. 23, 2002

(65) Prior Publication Data

US 2004/0017879 A1    Jan. 29, 2004

(51) Int. Cl.
*G01N 23/00* (2006.01)

(52) U.S. Cl. ............................. 378/5; 378/19
(58) Field of Classification Search ............... 378/5, 378/19
See application file for complete search history.

(56) References Cited

U.S. PATENT DOCUMENTS

| | | | |
|---|---|---|---|
| 4,029,963 A * | 6/1977 | Alvarez et al. ............... 378/5 |
| 4,149,081 A | 4/1979 | Seppi | |
| 4,241,404 A * | 12/1980 | Lux ............................ 378/2 |
| 4,255,664 A | 3/1981 | Rutt et al. | |
| 4,399,550 A * | 8/1983 | Hauck et al. ................ 378/5 |
| 4,511,799 A * | 4/1985 | Bjorkholm ................ 250/367 |
| 4,662,379 A | 5/1987 | Macovski | |
| 4,686,695 A * | 8/1987 | Macovski ................... 378/146 |
| 4,963,746 A | 10/1990 | Morgan et al. | |
| 5,262,946 A | 11/1993 | Heuscher | |
| 5,396,418 A | 3/1995 | Heuscher | |
| 5,485,493 A | 1/1996 | Heuscher et al. | |
| 5,533,080 A * | 7/1996 | Pelc ............................ 378/5 |
| 5,544,212 A | 8/1996 | Heuscher | |
| 5,570,403 A * | 10/1996 | Yamazaki et al. ............. 378/5 |
| 5,657,364 A | 8/1997 | Pfoh | |
| 5,748,705 A | 5/1998 | Stein et al. | |
| 5,778,045 A | 7/1998 | von Stetten et al. | |
| 5,835,555 A | 11/1998 | Barry et al. | |
| 6,217,214 B1 | 4/2001 | Cabral et al. | |
| 6,320,929 B1 * | 11/2001 | Von Der Haar ............... 378/4 |
| RE37,536 E | 2/2002 | Barnes | |
| 6,418,189 B1 | 7/2002 | Schafer | |
| 6,639,965 B1 * | 10/2003 | Hsieh et al. ................ 378/8 |

FOREIGN PATENT DOCUMENTS

EP          0211956          4/1987

\* cited by examiner

*Primary Examiner*—Craig E. Church
(74) *Attorney, Agent, or Firm*—Carl B. Horton, Esq.; Armstrong Teasdale LLP (57) ABSTRACT

A computed tomographic (CT) imaging system for performing a CT scan includes a detector array including a plurality of detector cells and a processor operationally coupled to the detector array. The processor is configured to receive first data regarding a first x-ray spectral range from a first detector cell, receive second data regarding a second x-ray spectral range different from the first x-ray spectral range from a second detector cell different from the first detector cell, and determine spectral information from the first data and the second data.

7 Claims, 13 Drawing Sheets

Any of the previous ideas along with a detector Design that can simultaneously measure two Different x-ray spectral ranges

Figure 14

METHODS AND APPARATUS FOR PERFORMING A COMPUTED TOMOGRAPHY SCAN

BACKGROUND OF INVENTION

This invention relates to computed tomographic (CT) imaging, and more particularly to methods and apparatus for measuring a spectral content and a total energy of an x-ray beam after attenuation by an object.

At least one known CT imaging system detector measures a current signal that is a representative of an energy of the x-ray beam received by the detector cells but does not measure both an energy of an x-ray beam and a spectral content of the x-ray beam after being attenuated by a patient.

SUMMARY OF INVENTION

In one aspect, a computed tomographic (CT) imaging system for performing a CT scan is provided. The CT system includes a detector array including a plurality of detector cells and a processor operationally coupled to the detector array. The processor is configured to receive first data regarding a first x-ray spectral range from a first detector cell, receive second data regarding a second x-ray spectral range different from the first x-ray spectral range from a second detector cell different from the first detector cell, and determine spectral information from the first data and the second data.

In another aspect, a method for scanning an object is provided. The method of scanning includes scanning an object by at least one of scanning the object while varying a peak kiloelectronvolt to an x-ray tube, scanning the object with a filter such that a plurality of x-ray spectra are received by a detector array, and scanning the object such that elements of a detector array discriminate between a plurality of x-ray spectra and generate signals based on the x-ray spectra.

In yet another aspect, a method for determining the presence of an analyte in an object with a computed tomographic (CT) imaging system is provided. The method includes receiving first data regarding a first x-ray spectral range from a first detector cell, receiving second data regarding a second x-ray spectral range different from the first x-ray spectral range from a second detector cell different from the first detector cell, and determining spectral information from the first data and the second data.

In still another aspect, a computed tomographic (CT) imaging system for performing a CT scan is provided. The CT system includes a detector array including a plurality of detector cells, an x-ray source positioned to emit x-rays toward the detector array, a plurality of x-ray energy filter elements separated by intervening air paths and oriented in a Z direction, and a processor operationally coupled to the detector array. The processor is configured to receive first data regarding a first x-ray spectral range from a first detector cell, receive second data regarding a second x-ray spectral range different from the first x-ray spectral range from a second detector cell different from the first detector cell, and determine spectral information from the first data and the second data.

DETAILED DESCRIPTION

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a helical scan may be performed. To perform a helical scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The helical weighting algorithms also scale the data according to a scaling factor, which is a function of the distance between the x-ray source and the object. The weighted and scaled data is then processed to generate CT numbers and to construct an image that corresponds to a two dimensional slice taken through the object.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
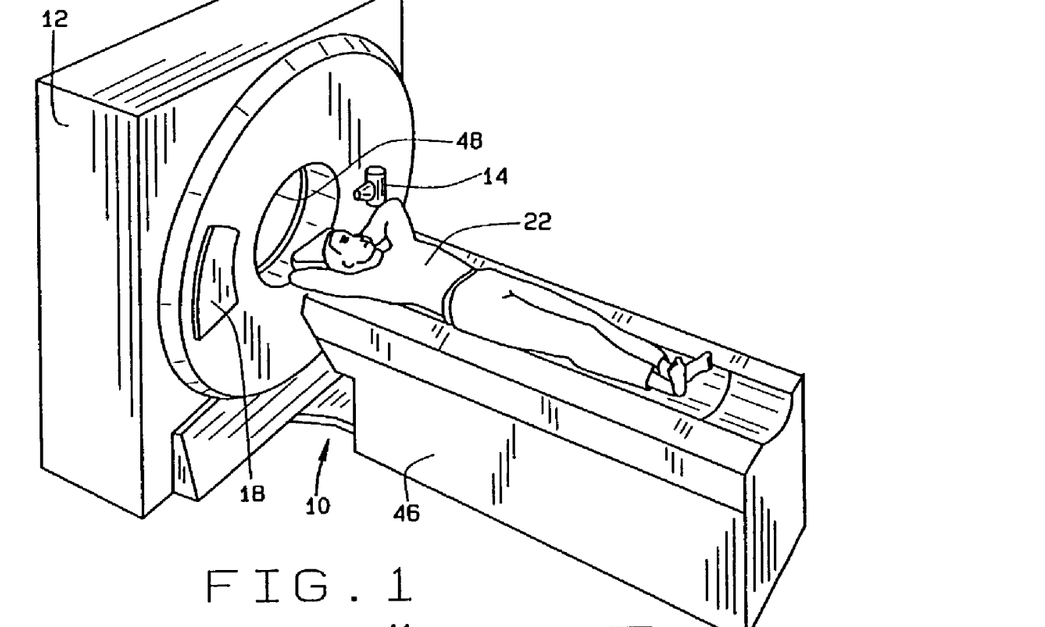
FIG. 1 is a pictorial view of a CT imaging system.
Figure 2:
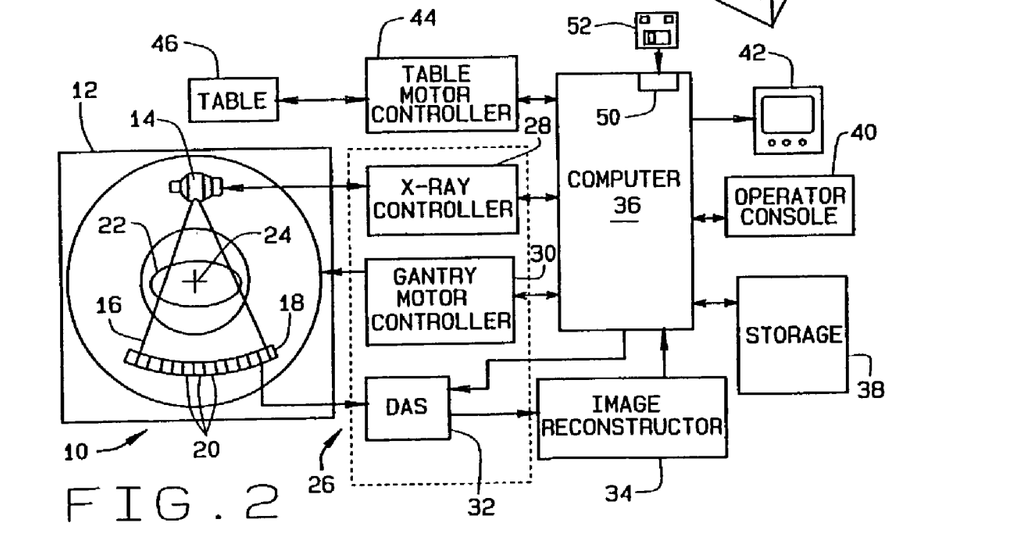
FIG. 2 is a block schematic diagram of the system illustrated in FIG. 1.

Referring to FIGS. 1 and 2, a multi-slice scanning imaging system, for example, a computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Figure 3:
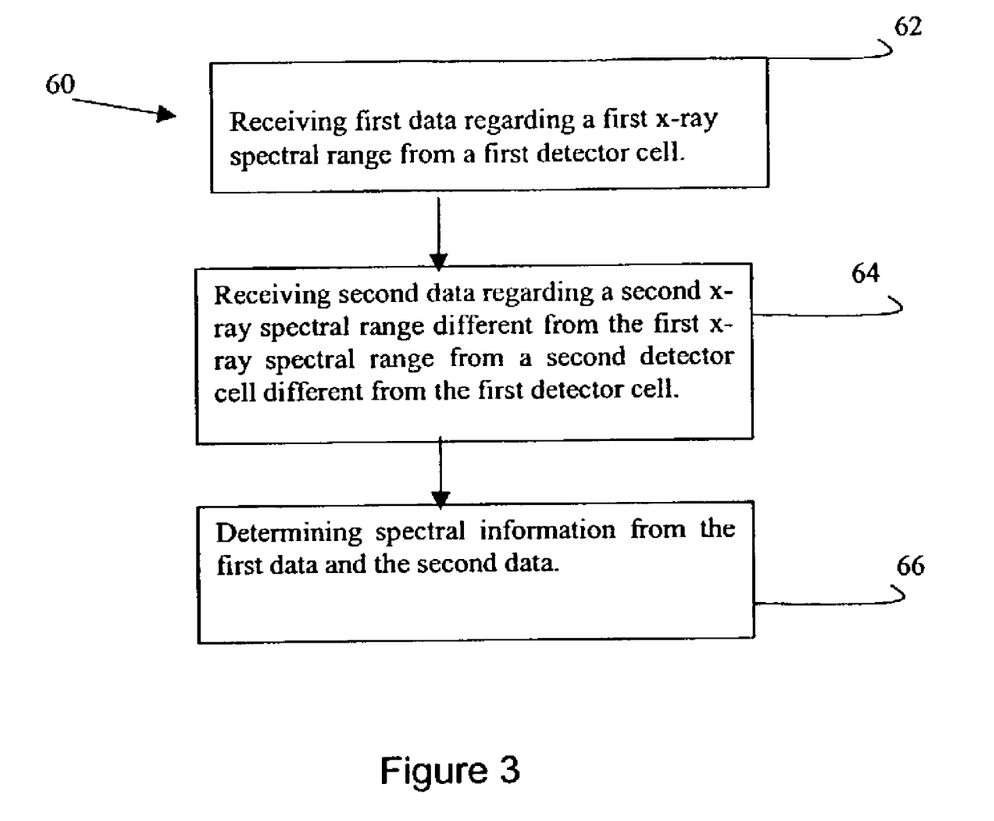
FIG. 3 illustrates a method for performing a computed tomography (CT) scan.

FIG. 3 illustrates a method 60 for performing a computed tomography (CT) scan. In one embodiment, method 60 includes receiving 62 first data regarding a first x-ray spectral range from a first detector cell 20, receiving 64 second data regarding a second x-ray spectral range different from the first x-ray spectral range from a second detector cell 20 different from the first detector cell 20, and determining 66 spectral information from the first data and the second data.

Figure 4:
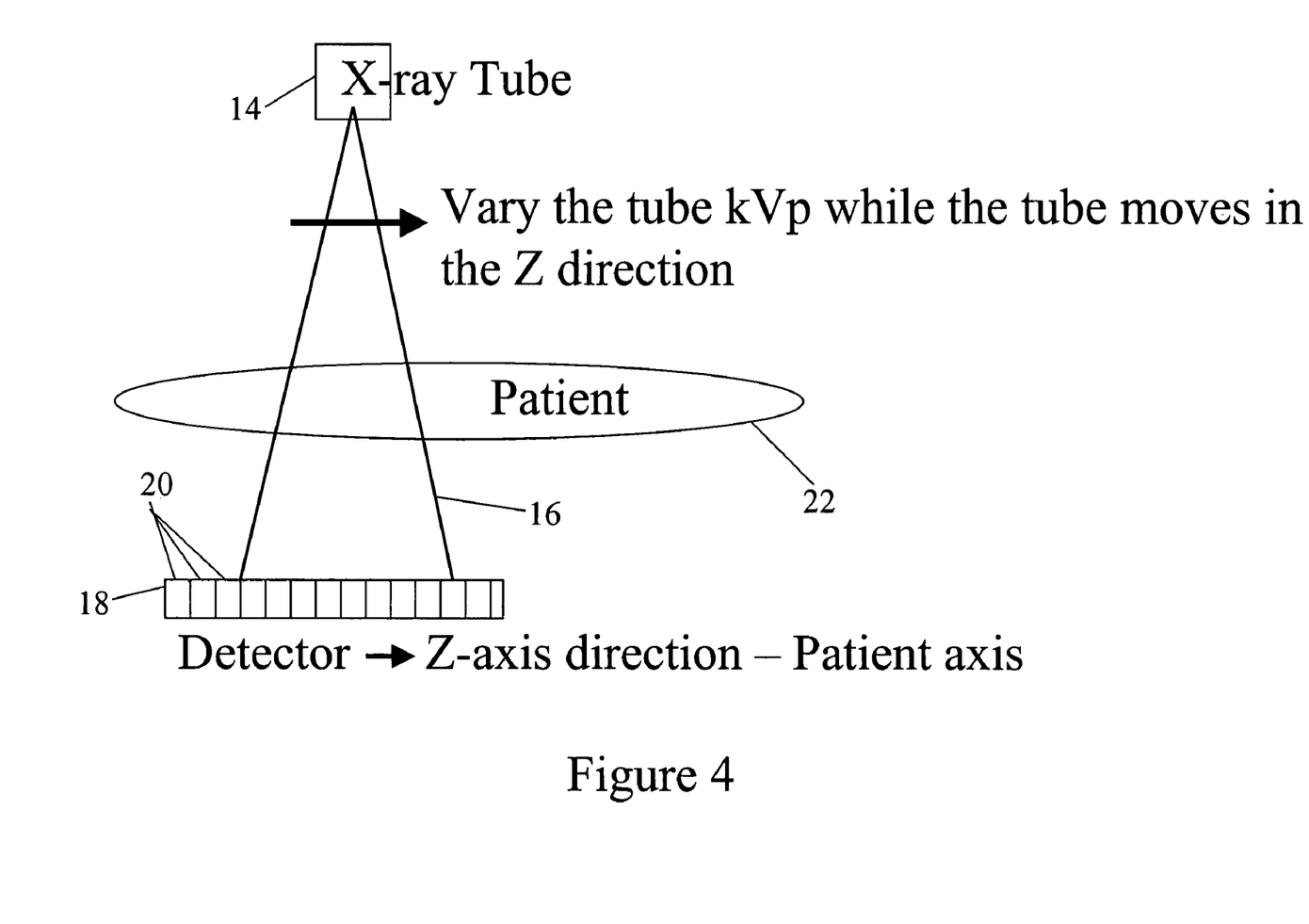
FIG. 4 illustrates an x-ray tube in which a kVp is varied in a Z direction.

FIG. 4 illustrates an x-ray tube 14 in which a kVp (peak kiloelectronvolt) is varied as the tube is moved in a Z direction. In one embodiment, method 60 includes using x-ray beam 16 including a spatially variant x-ray energy distribution in a Z direction. The spatially variant x-ray energy distribution in the Z direction is generated using an obtuse angle off an x-ray source target that includes a highly varying x-ray self absorption by the x-ray source target. In one embodiment, varying the x-ray source 14 in the Z direction produces images of object 22 in which each detector row corresponds to attenuation data from a different x-ray subspectrum and from which a plurality of spectral information about object 22 can be obtained. As used herein, subspectra and subspectrum can mean the full x-ray spectrum or any subpart thereof. Determining spectral information means taking a difference between two or more x-ray attenuation measurements collected with a plurality of x-ray subspectra. For example, the x-ray source is constructed such that when energized the x-ray source emits x-rays such that there is a spatially variant x-ray spectral distribution in the Z direction and a first detector row receives x-rays of a different spectrum than received at a second detector row. The data samples thus received from the first and second detector rows are then analyzed to determine the presence of a particular analyte. As used herein analyte refers to a specific material in an object such as a patient that one desires to identify such as bone, calcium, iodine or other contrast agent, and other types of agents or dyes that provide functional information and/or anatomical information.

Figure 5:
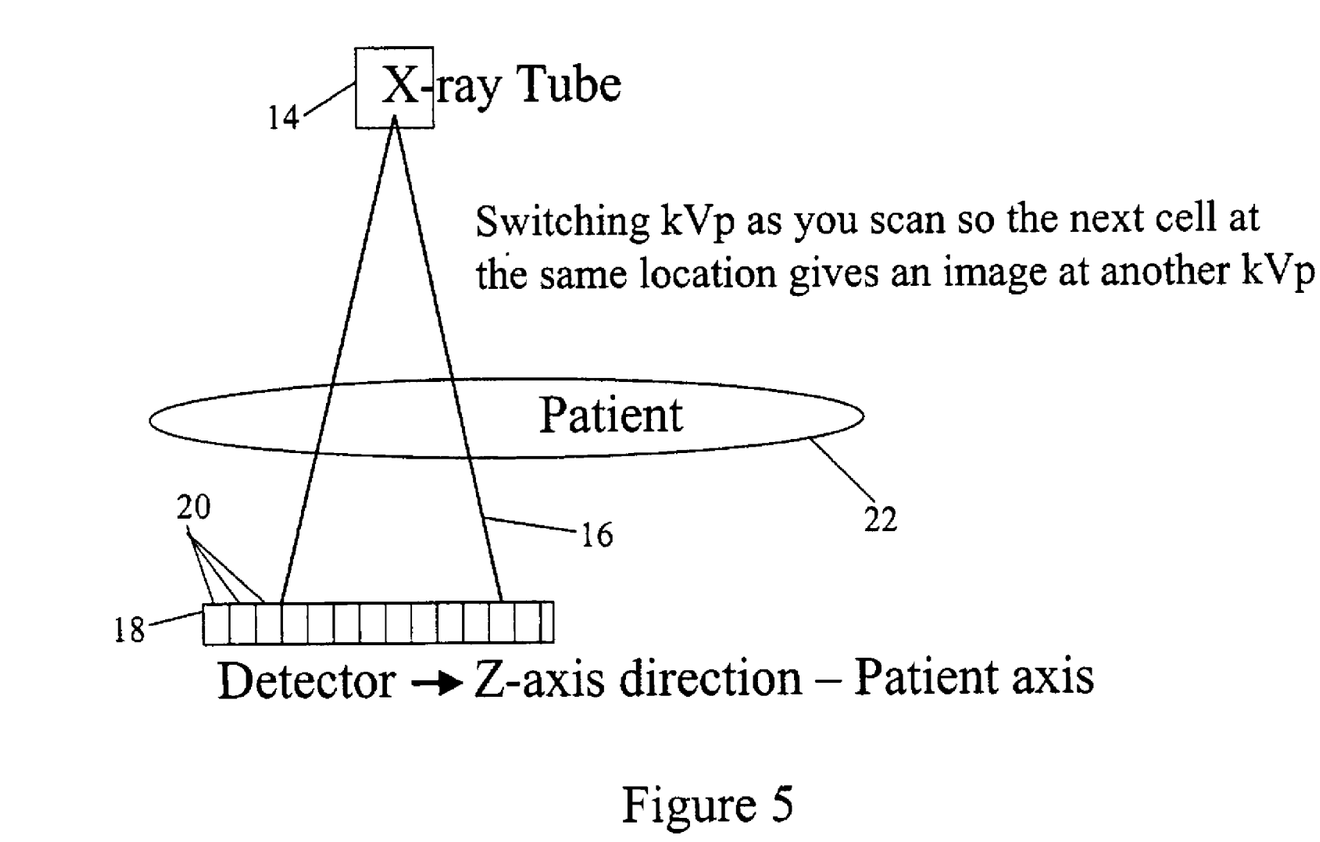
FIG. 5 illustrates an x-ray tube which is switched between a plurality of different kVp's during a scan.

FIG. 5 illustrates an x-ray tube 14 which is switched between a plurality of different kVp's during a scan. Switching the x-ray tube kVp in turn alters the x-ray spectrum emitted by x-ray tube 14. In this embodiment, the spatially variant x-ray energy distribution in the Z direction is generated by varying the x-ray source tube kVp for each rotation or half slice of data. For example, using an eight slice detector, eight different kvp's are cycled. Method 60 facilitates running continuous helical to obtain a continuous stream of slice data that includes elemental composition data in specific areas of interest of object 22. For example, the x-ray source tube is energized at a first kVp when object 22 is at a first detector row to obtain a first data sample. The x-ray source is then energized at a second kVp when object 22 is at a different detector row to obtain a second data sample. The two data samples are then analyzed to determine the presence of a particular analyte. Accordingly, attenuation data obtained at two different subspectra of radiation are compared to determine a presence of the analyte.

Figure 14:
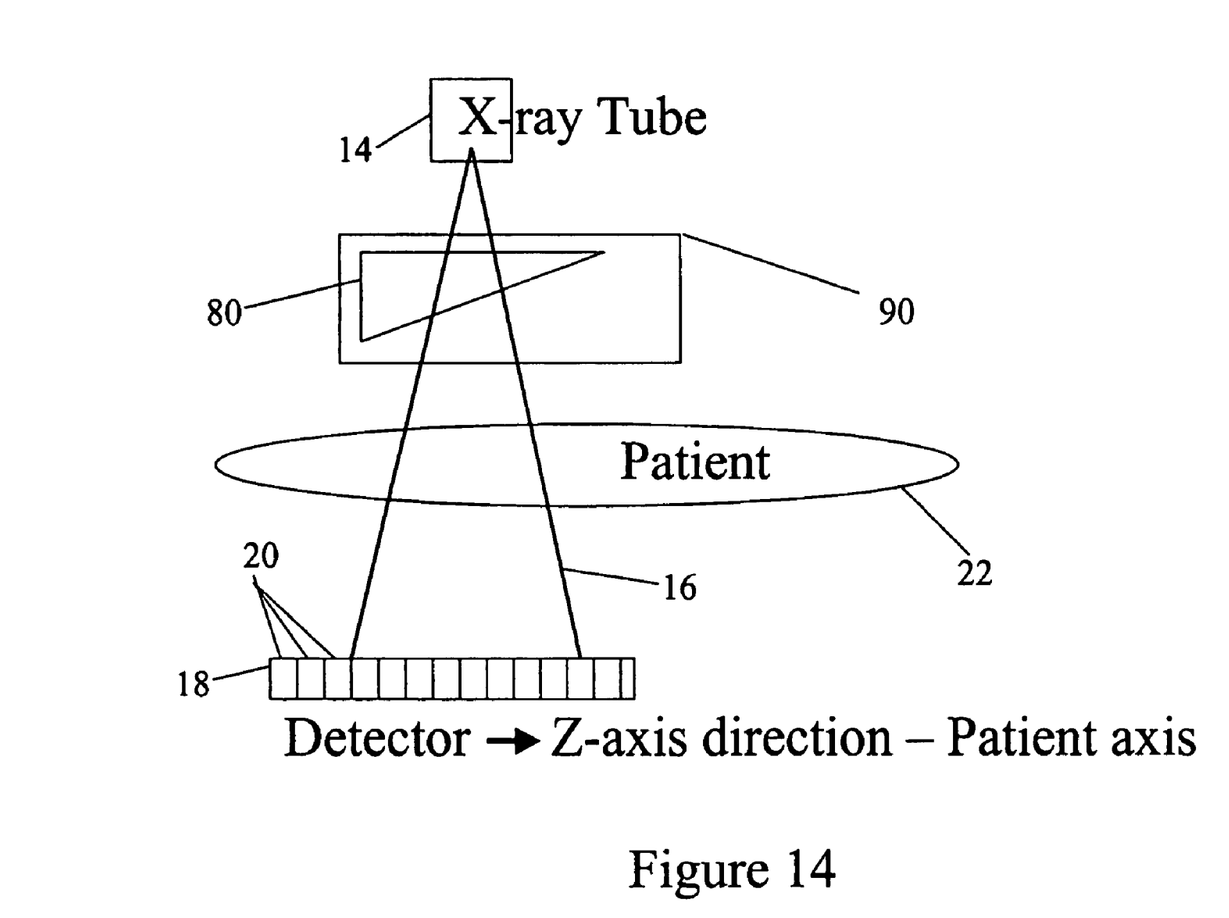
FIG. 14 illustrates a filter positioned in a collimator.

In another embodiment, method 60 includes positioning a shaped x-ray filter in a Z direction between x-ray source 14 and a collimator 90 (shown in FIG. 14). In one embodiment, the filter includes, but is not limited to, a simple stepped filter, a sloped filter per Z location or per detector cell in the Z direction, a set of K edge filters per Z location, a set of paired K edge filters per Z location, or more elaborate and complicated designs. In another embodiment, the filter is positioned in collimator 90. Gantry 12, including x-ray source 14, is then rotated about object 22 using an x-ray source pitch of one detector cell such that each detector cell 20 of detector 18 images the same slice of object 22 using a different x-ray spectrum. For example, using imaging system 10 including an eight slice detector, method 60 generates eight overlapping images each created with a different energy x-ray beam. The data from each of these eight slices is then analyzed to determine the spectral content associated with the anatomical CT slice data.

Figure 6:
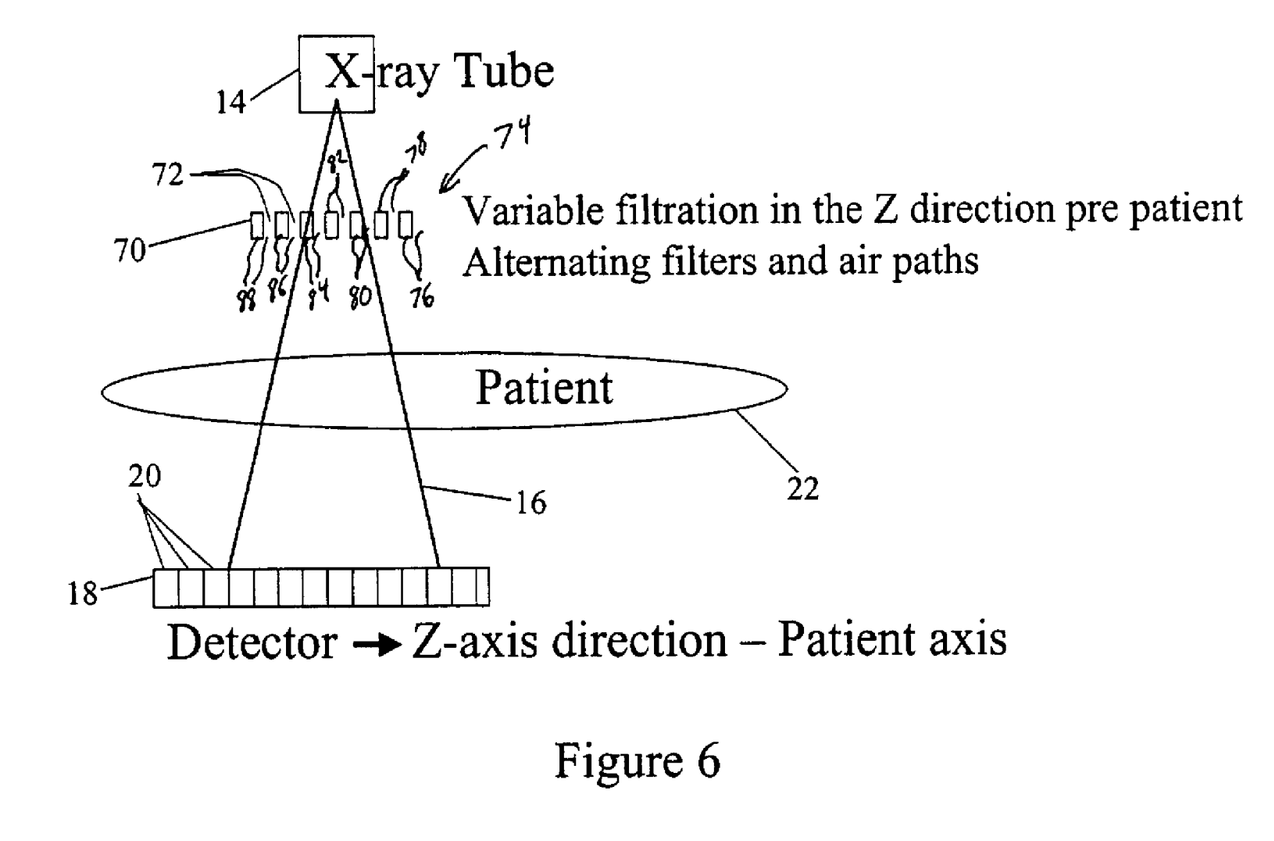
FIG. 6 illustrates an x-ray beam subjected to a variable filtration in a Z direction pre-patient, with a plurality of alternating filters and air paths.
Figure 7:
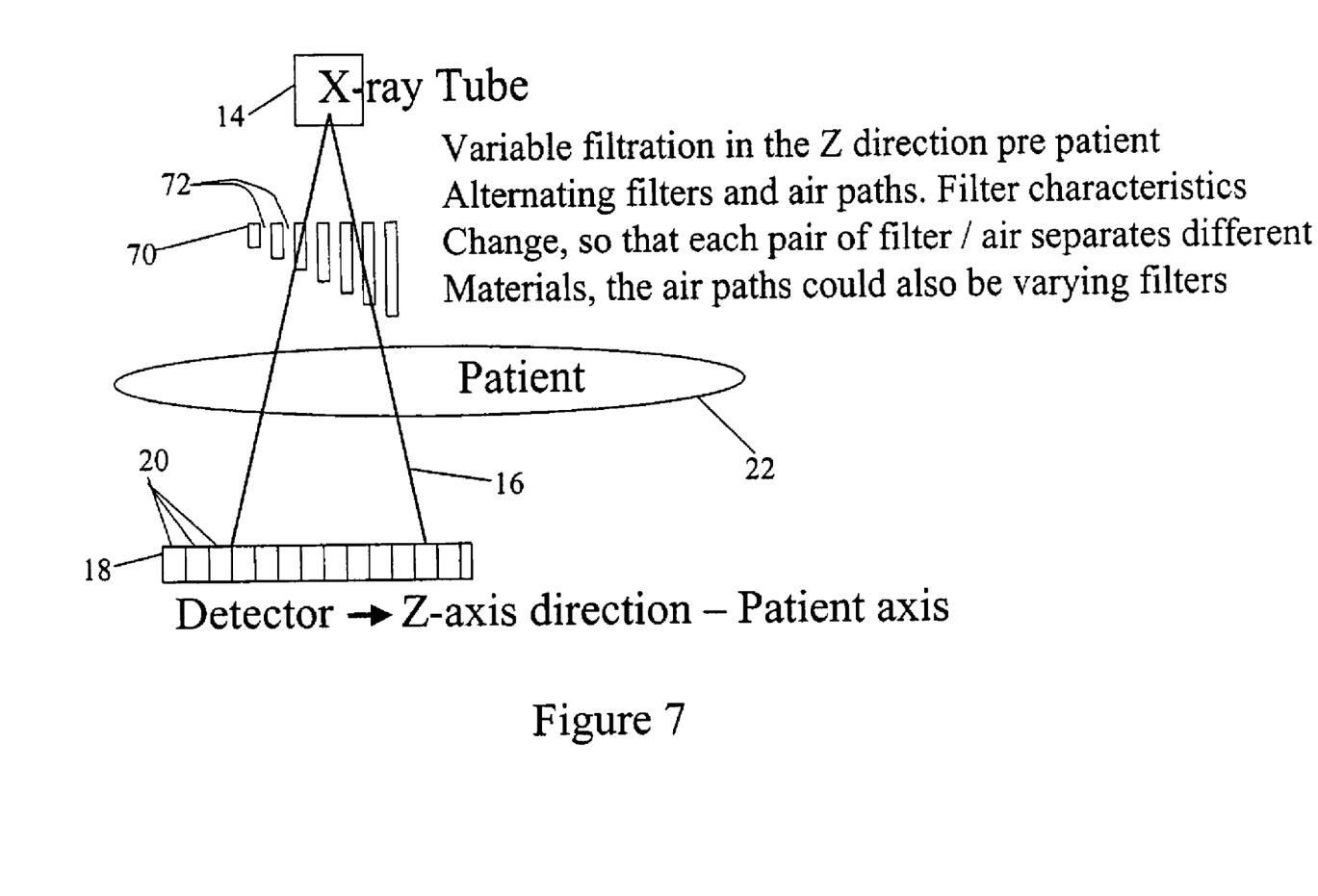
FIG. 7 illustrates an x-ray beam subjected to a variable filtration in a Z direction pre-patient, with a plurality of alternating filters and air paths.

FIG. 6 illustrates an x-ray beam 16 subjected to a variable filtration in a Z direction before reaching object 22, with a plurality of alternating filters 70 and air paths 72. In one embodiment, a plurality of filters 70 are alternated with air paths 72 such that individual detector rows receive filtered or unfiltered x-ray beam data. Attenuation data from filtered and unfiltered x-ray beams is subsequently analyzed to determine a spectral content associated with anatomical CT slice data. Filters 70 may all have the same characteristics, as shown in FIG. 6, or may have different characteristics, as depicted in FIG. 7. Also illustrated in FIG. 6 are a plurality of filter-plus-air-path pairs 74 including a first pair 76, a second pair 78, a third pair 80, a fourth pair 82, a fifth pair 84, a sixth pair 86, and a seventh pair 88. As patient 22 and filter-plus-air-path pairs 74 move relative to each other in the Z direction, dynamic information is obtainable. For example, an analyte is injected or otherwise provided in patient 22 at or near an area of interest, and first pair 74 passes over the area of interest at a first time $T_0$. Detector 18 receives attenuated x-rays at time $T_0$ and a first spectral analysis determines the location of the analyte at $T_0$. While the relative motion in Z continues, second pair 78 passes over the area of interest at a later time than time $T_0$, say time $T_1$, and a second spectral analysis determines the location of the analyte at $T_1$. Additionally, third pair 80 through seventh pair 88, pass over the area of interest at times $T_2$ though $T_6$, and spectral analyses allow for the determination of the analyte's location at times $T_2$ through $T_6$. By knowing the analyte's location at the various times, dynamic information regarding the analyte's movement thought patient's 22 body is provided. Although illustrated with seven filter-plus-air-path pairs 74, it is contemplated that the benefits of the invention accrue to embodiments with more than and less than seven pairs.

FIG. 7 illustrates an x-ray beam 16 subjected to a variable filtration in a Z direction before reaching object 22, with a plurality of alternating filters 70 and air paths 72 to analyze different materials. The filter-plus-air-path pairs in this embodiment are designed to detect such analytes including, but not limited to, bone, calcium, iodine or other contrast agent, and other types of agents or dyes that provide functional information and/or anatomical information.

Figure 8:
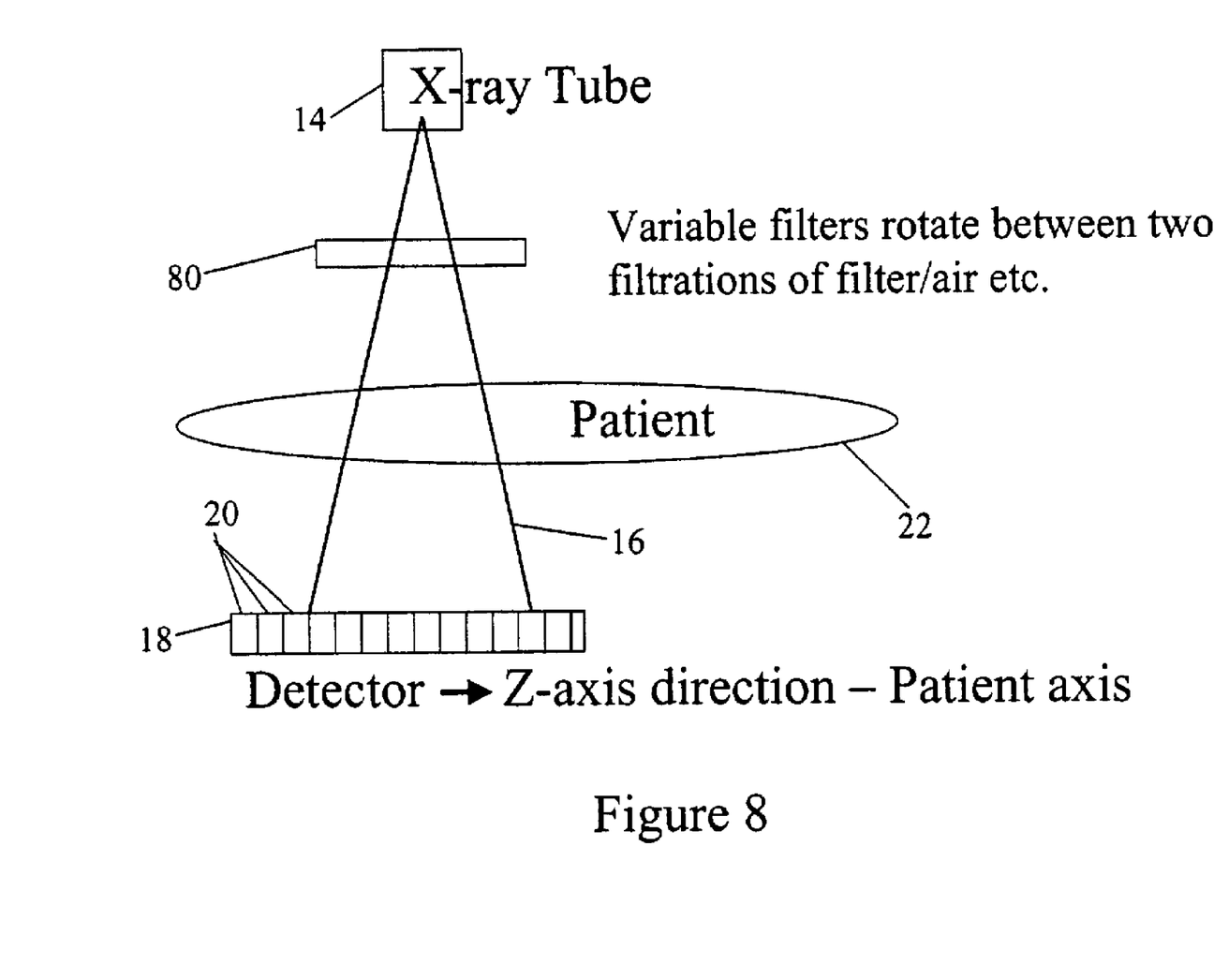
FIG. 8 illustrates an x-ray beam subjected to variable filtration in a Z direction pre-patient, with a plurality of variable filters which rotate between two or more filter/air positions.
Figure 9:
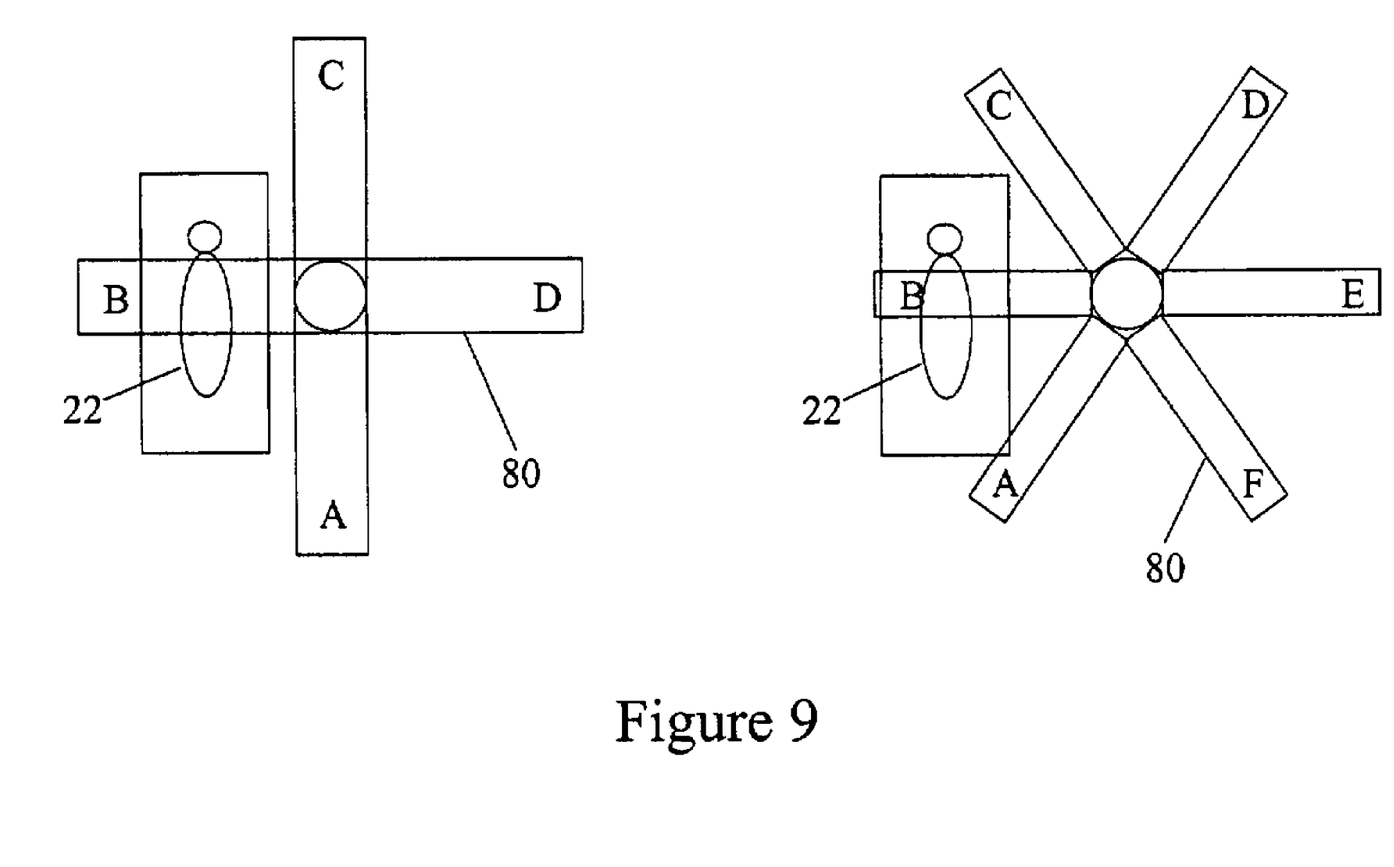
FIG. 9 illustrates two variable filter configurations as seen from the perspective of looking down toward the patient.
Figure 10:
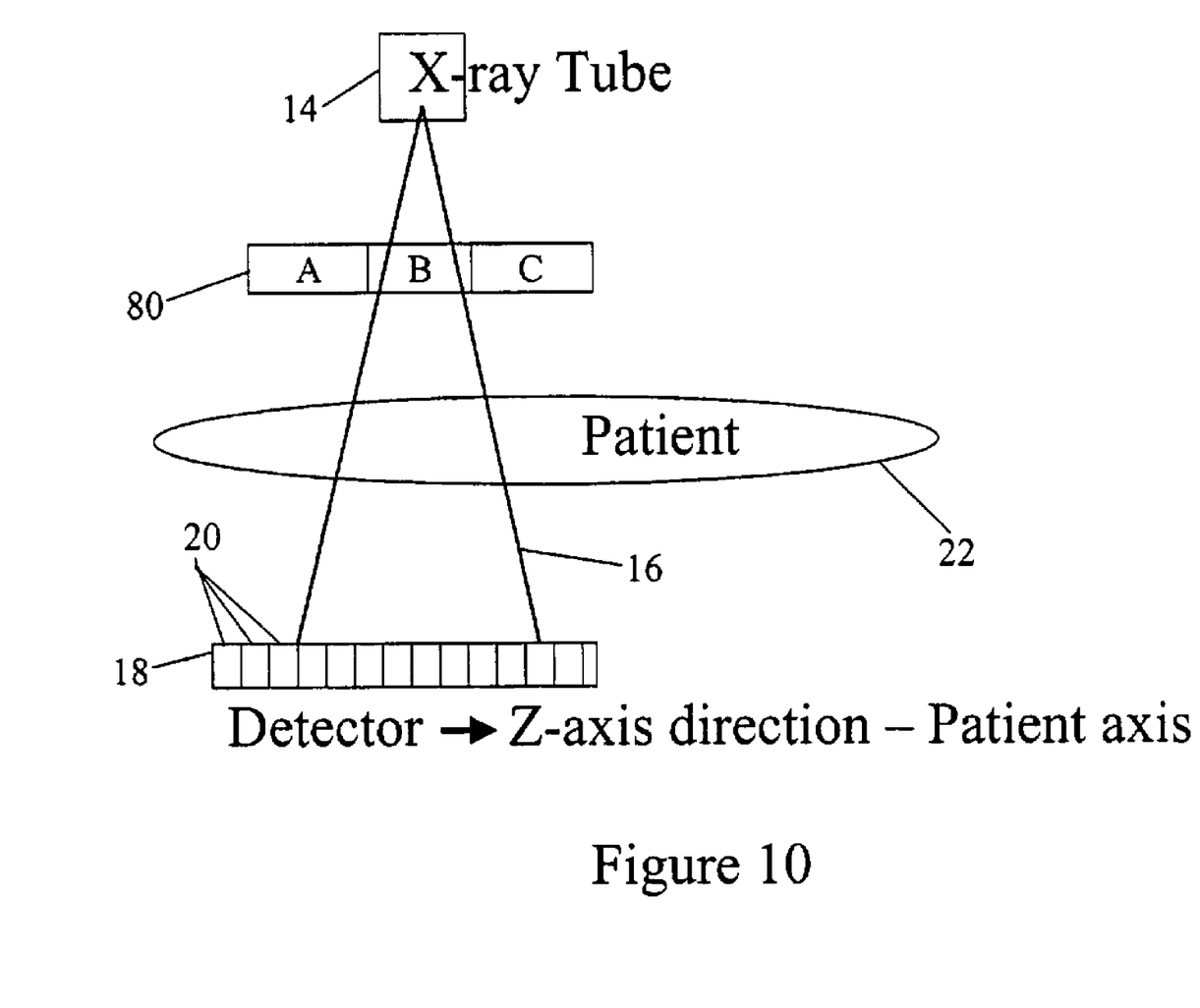
FIG. 10 illustrates an x-ray beam subjected to variable filtration in a Z direction pre-patient, with a variable filter comprising a plurality of distinct parts each of which has different x-ray filtration properties.
Figure 11:
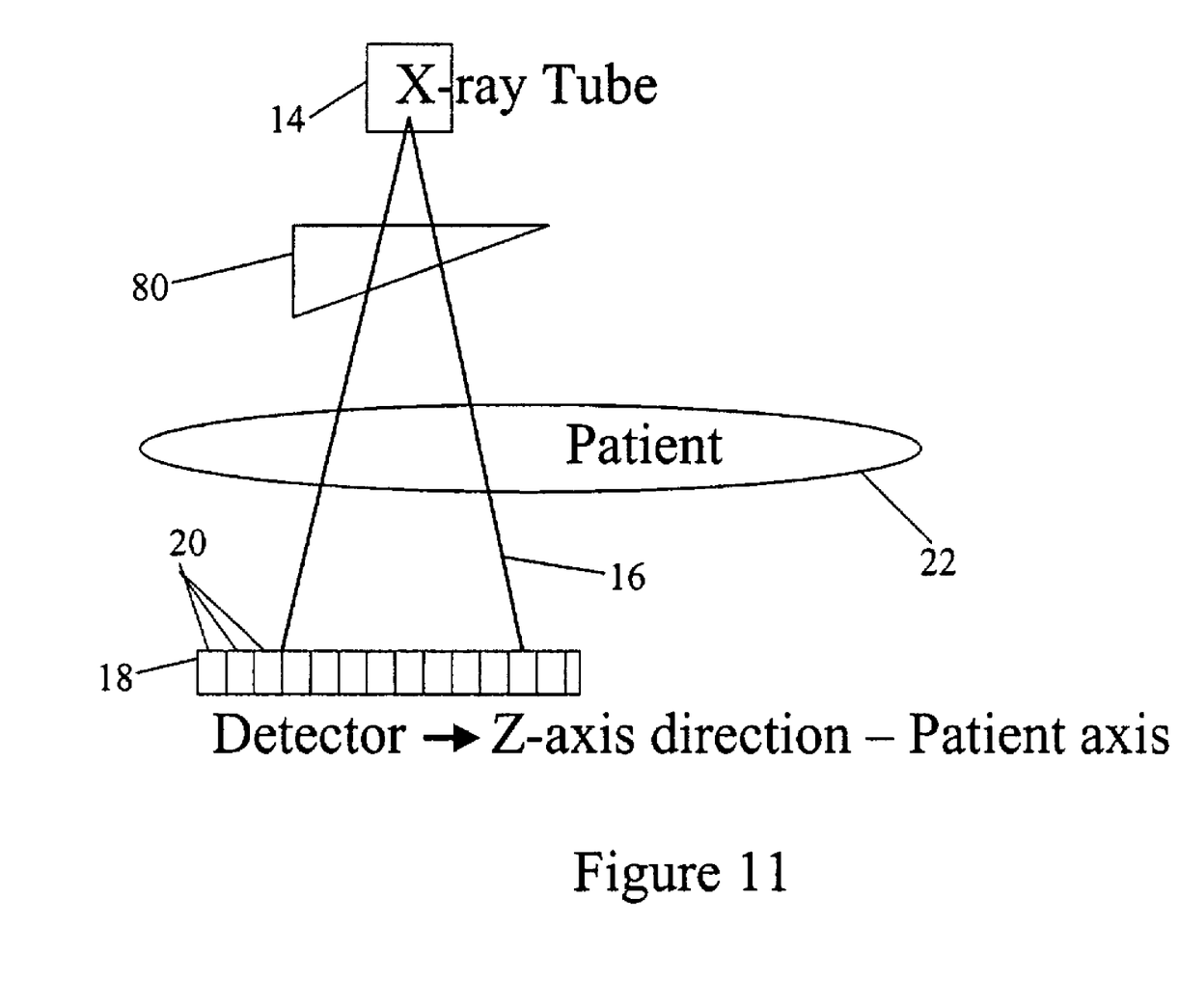
FIG. 11 illustrates an x-ray beam subjected to variable filtration in a Z direction pre-patient, with a variable filter comprising a wedge-shaped block that has x-ray filtration properties that vary in a Z direction.

FIG. 8 illustrates an x-ray beam subjected to variable filtration in a Z direction before reaching object 22. In one embodiment, at least one variable filter 80 rotates between a plurality of filter/air positions. Variable filter 80 comprises a plurality of discrete x-ray filters that rotate into position between x-ray source 14 and object 22. FIG. 9 illustrates two variable filter configurations as seen from the perspective of looking down toward object 22. In another embodiment variable filter 80 comprises a stationary filter that has x-ray filtration properties which vary along the Z direction. In yet another embodiment, variable filter 80 is drum shaped including at least one filter section and at least one slit providing an air path. Alternatively, drum shaped variable filter 80 includes a plurality of filter sections with different filter characteristics. FIG. 10 illustrates an x-ray beam 16 subjected to variable filtration in a Z direction between x-ray source 14 and object 22, with variable filter 80 comprising a plurality of distinct parts each of which has different x-ray filtration properties. FIG. 11 illustrates an x-ray beam 16 subjected to variable filtration in a Z direction between x-ray source 14 and object 22, with variable filter 80 being a wedge-shaped block of a single substance wherein the x-ray filtration properties vary in the Z direction based solely on thickness.

Figure 12:
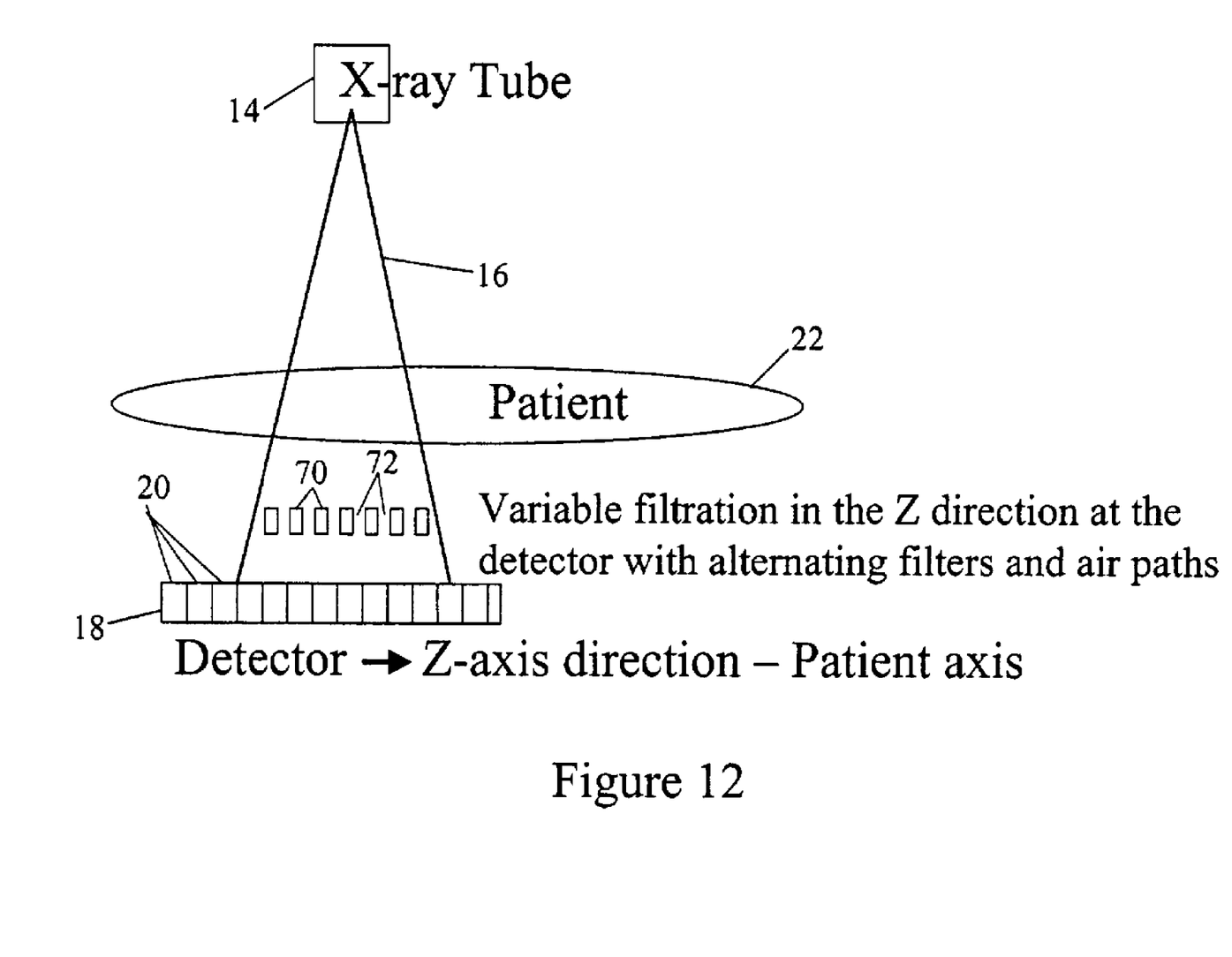
FIG. 12 illustrates an x-ray beam subjected to variable filtration in a Z direction between an object and a detector, with a plurality of alternating filters and air paths to separate different materials.

FIG. 12 illustrates an x-ray beam 16 subjected to variable filtration in a Z direction between object 22 and detector 18, with a plurality of alternating filters 70 and air paths 72 to analyze different materials. In one embodiment, a plurality of filters 70 are alternated with air paths 72 such that individual detector rows receive x-ray data that is filtered or unfiltered after being attenuated by object 22. Attenuation data from filtered and unfiltered x-ray beams is subsequently analyzed to determine a spectral content associated with anatomical CT slice data. The filter-plus-air-path pairs in this embodiment are designed to detect such analytes including, but not limited to, calcium, bone, iodine or other contrast agent, and other types of agents or dyes that provide functional information and/or anatomical information.

Figure 13:
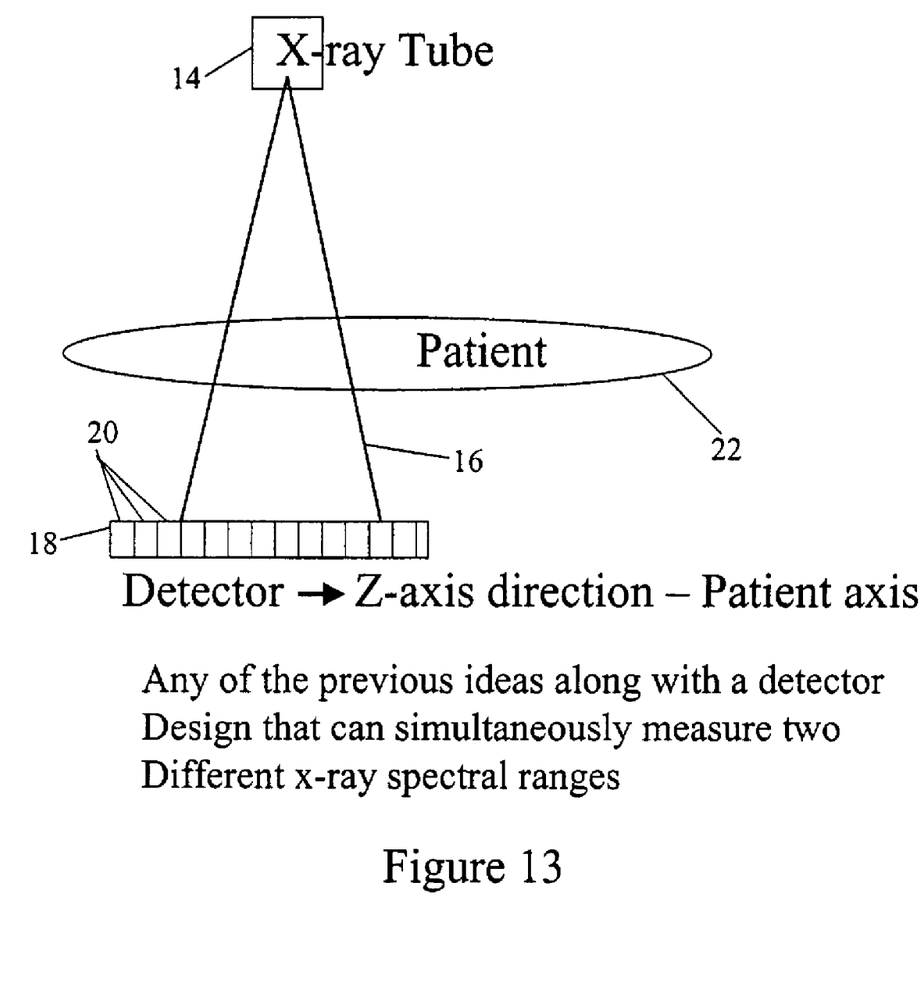
FIG. 13 illustrates a detector which simultaneously measures a plurality of different x-ray spectral ranges.

FIG. 13 illustrates a detector 18 which simultaneously measures a plurality of different x-ray spectral ranges. In use, detector cells 20 can distinguish between x-ray spectra through means including, but not limited to, the use of a filter in front of each cell 20 or a cell variation which lends itself to detecting various x-ray energies so as to make detector cell 20 self-discriminating. In other words, detector cells 20 selectively respond to different x-ray subspectra and no filters are used. Detector cells 20 are made self-discriminating by methods including, but not limited to, manufacturing detector cells 20 from different materials that are sensitive to different portions of the x-ray spectrum and coating each detector cell 20 with a different scintillating material that is sensitive to a different portion of the x-ray spectrum.

In another embodiment, an effective x-ray source current (in milliamperes) is reduced for each slice to facilitate preventing an increased accumulated x-ray dose per CT slice. In use, the reduced x-ray source current can be used with a radio opaque contrast agent, such as, but not limited to, iodine, to gather dynamic information. Further, all eight slices of an eight slice detector can be used in this method. Alternatively, two sets of four slices of the eight slice detector can be used to generate multiple sets of data per detector 18. Detectors with a higher number of cells 20, i.e. sixteen or more, can have an even greater advantage in this operating mode. In another embodiment, detector 18 is designed to gather spectral information directly through the use of a filter in front of each cell 20, or a cell variation which facilitates detecting various X-ray energies can be used. For example, method 60 as describe herein can be used on a plurality of combinations of systems and detectors, and can also be combined, such as utilizing both pre-patient and post patient spectral discrimination hardware etc.

Measuring both an energy of an x-ray beam and a spectral content of the x-ray beam after being attenuated by a patient facilitates allowing a two-dimensional (2D) determination of both an anatomical composition and elemental composition within a CT slice. Multiple samples taken over time also facilitate allowing a plurality of dynamic flow studies, such as, but not limited to, tracking an iodine contrast media perfusion or a blood flow study. Additionally, spectral content information obtained from a plurality of detector cells can be used to correct for beam hardening, thereby obtaining CT numbers with an increased accuracy.

While the invention has been described in terms of various specific embodiments, those skilled in the art will recognize that the invention can be practiced with modification within the spirit and scope of the claims.

The invention claimed is:

1. A computed tomographic (CT) imaging system for performing a CT scan, said CT system comprising:
   an x-ray source emitting a spectrum of x-rays;
   a detector array comprising a plurality of detector cells arranged in rows, said detector array including detector cells that are at least one of manufactured from different materials that are sensitive to different portions of the x-ray spectrum or coated with different scintillating materials that are sensitive to a different portion of the x-ray spectrum;
   a plurality of alternating discrete filters and air paths in pairs oriented in a Z-direction configured so that individual detector rows receive filtered or unfiltered x-ray beam data;
   a gantry for rotating said x-ray source and said detector array;
   a table for translating an object between said x-ray source and said detector array; and
   a processor operationally coupled to said detector array, and as an object being imaged and said filter and air path pairs move relative to one another in the Z-direction, said processor configured to:
   receive first data regarding a first x-ray spectral range from a first detector cell from a scan with an x-ray source pitch of one detector cell such that the x-ray source advances relative to the table one detector cell per revolution;
   receive second data regarding a second x-ray spectral range different from the first x-ray spectral range from a second detector cell different from the first detector cell;
   perform a first spectral analysis at a time $T_0$ using said first data and said second data to determine a location of an analyte in an area of interest in the object being imaged; and
   as said relative motion in a Z-direction continues, perform subsequent spectral analyses using different said filter and air path pairs to determine dynamic information of the movement of the analyte.

2. A CT system in accordance with claim 1 wherein said first detector cell detects a different x-ray subspectrum than said second detector cell.

3. A CT system in accordance with claim 1 wherein one of said discrete filters has a first x-ray absorption property and one of said discrete filters has a second x-ray absorption property different from the first.

4. A CT system in accordance with claim 1 wherein said discrete filters each have substantially the same x-ray absorption property.

5. A CT system in accordance with claim 1 wherein said filters of said plurality of alternating discrete filters and air paths in pairs oriented in a Z-direction are positioned between said x-ray source and the object being imaged.

6. A CT system in accordance with claim 1 wherein said filters of said plurality of alternating discrete filters and air paths in pairs oriented in a Z-direction are positioned in an x-ray collimator between said x-ray source and the object being imaged.

7. A method for determining the presence of an analyte in an object with a computed tomographic (CT) imaging system having a detector array comprising a plurality of detector cells arranged in rows, said detector array including detector cells that are at least one of manufactured from different materials that are sensitive to different portions of the x-ray spectrum or coated with different scintillating materials that are sensitive to a different portion of the x-ray spectrum and said imaging system further having a plurality of alternating discrete filters and air paths in pairs oriented in a Z-direction configured so that individual detector rows receive filtered or unfiltered x-ray beam data,
   said method comprising:
   receiving first data regarding a first x-ray spectral range from a first detector cell from a scan with an x-ray source pitch of one detector cell such that the x-ray source advances one detector cell per revolution;
   receiving second data regarding a second x-ray spectral range different from the first x-ray spectral range from a second detector cell different from the first detector cell and the second detector cell at least one of manufactured from a different material sensitive to different portions of the x-ray spectrum from the first detector cell or coated with a different scintillating material sensitive to a different portion of the x-ray spectrum than the first detector cell;
   performing a first spectral analysis at a time $T_0$ using said first data and said second data to determine a location of an analyte in an area of interest in an object being imaged and moved in the Z-direction relative to the filter and air path pairs; and
   as relative motion in a Z-direction continues, performing subsequent spectral analyses using different said filter and air path pairs to determine dynamic information of the movement of the analyte.

* * * * *